United States Patent [19]  [11] Patent Number: 4,605,620
Andersch et al.  [45] Date of Patent: Aug. 12, 1986

[54] PROCESS FOR FERMENTING CARBOHYDRATE- AND PHOSPHATE-CONTAINING LIQUID MEDIA

[75] Inventors: Wolfram Andersch, Hildesheim; Hubert Bahl, Essen-Oldenburg; Gerhard Gottschalk, Nörten-Hardenberg, all of Fed. Rep. of Germany

[73] Assignee: Gesellschaft fur Biotechnologische Forschung mbH (GBF), Braunschweig-Stockheim, Fed. Rep. of Germany

[21] Appl. No.: 442,093

[22] Filed: Nov. 16, 1982

[30] Foreign Application Priority Data

Nov. 20, 1981 [DE] Fed. Rep. of Germany ....... 3146084

[51] Int. Cl.$^4$ .......................... C12N 1/20; C12P 7/28; C12P 7/26; C12Q 3/00
[52] U.S. Cl. .................................. 435/148; 435/150; 435/160; 435/161; 435/253; 435/3
[58] Field of Search ................... 435/154, 3, 148, 150, 435/157, 160, 161, 253, 813, 842

[56] References Cited

U.S. PATENT DOCUMENTS

| | | | |
|---|---|---|---|
| 1,858,808 | 5/1932 | Gerretsen | 435/150 |
| 2,107,262 | 2/1938 | Legg et al. | 435/160 |
| 2,198,104 | 4/1940 | Carnarius | 435/150 |
| 3,062,724 | 11/1962 | Reusser | 435/75 |

FOREIGN PATENT DOCUMENTS 155329 6/1982 Fed. Rep. of Germany .......... 435/3

OTHER PUBLICATIONS

Bahl, H., et al., *Eur. J. Appl. Microbiol. Biotecnnol.*, vol. 15, pp. 201–205, 1982.
Abou–Zeid et al, *Indian Chemical Manufacturer*, vol. 17(1) pp. 15–21, 1979.
Abou–Zeid, A., et al., "Influence of Nitrogen Sources and Phosphorus on the Fermentative Production of Acetone and Butanol by *Clostridium Acetobutylicum*", Chem. Abst., vol. 91, 54574n (1979).

*Primary Examiner*—Thomas G. Wiseman
*Assistant Examiner*—Jayme A. Huleatt
*Attorney, Agent, or Firm*—Bierman, Peroff & Muserlian

[57] ABSTRACT

The invention relates to a process for fermenting carbohydrate- and phosphate-containing liquid media with limitation of phosphate with bacteria capable of forming butanol, acetone and/or ethanol as fermentation products performed with a total phosphate content in the medium of 1.0 to 0.4 mmoles.

8 Claims, 6 Drawing Figures

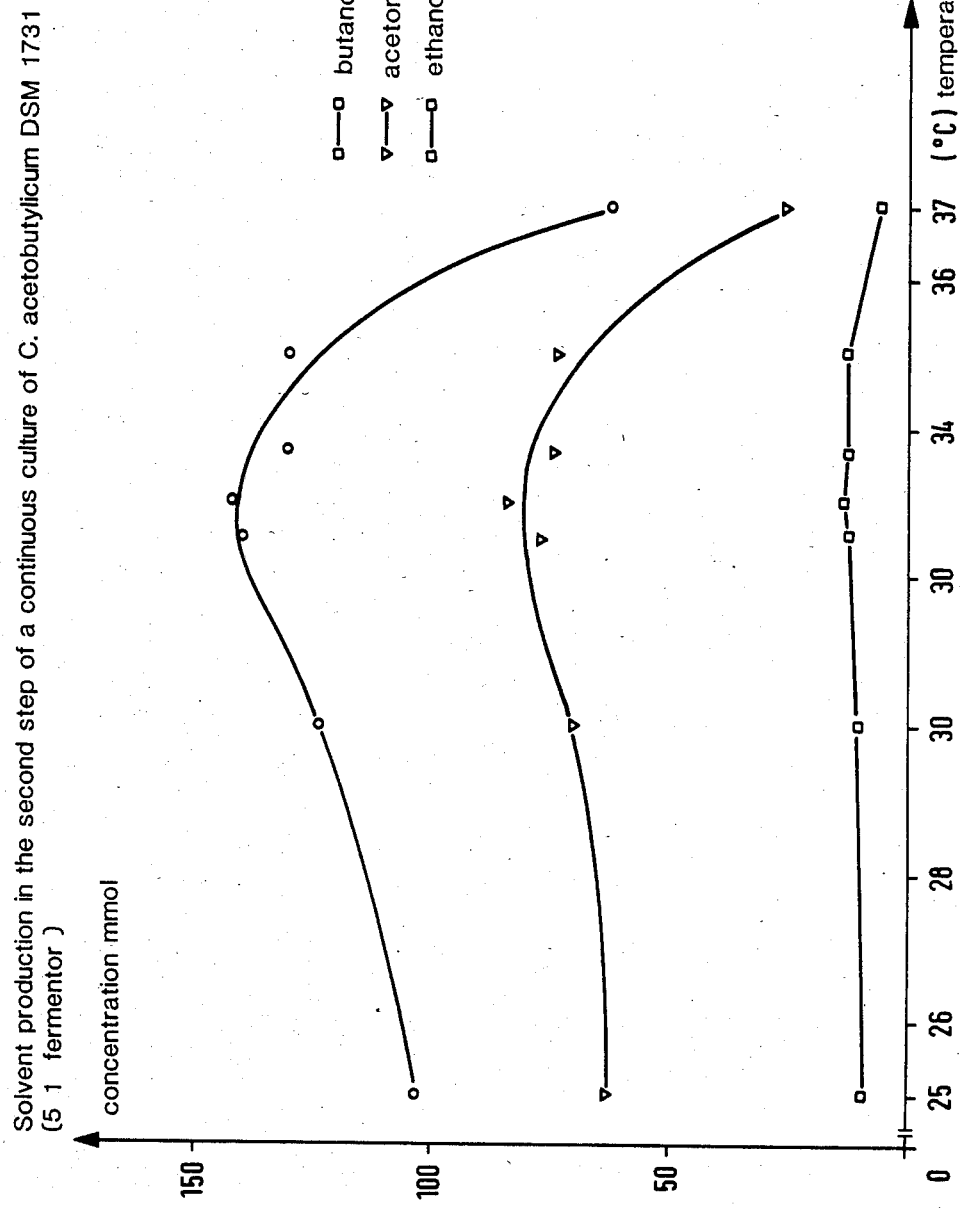

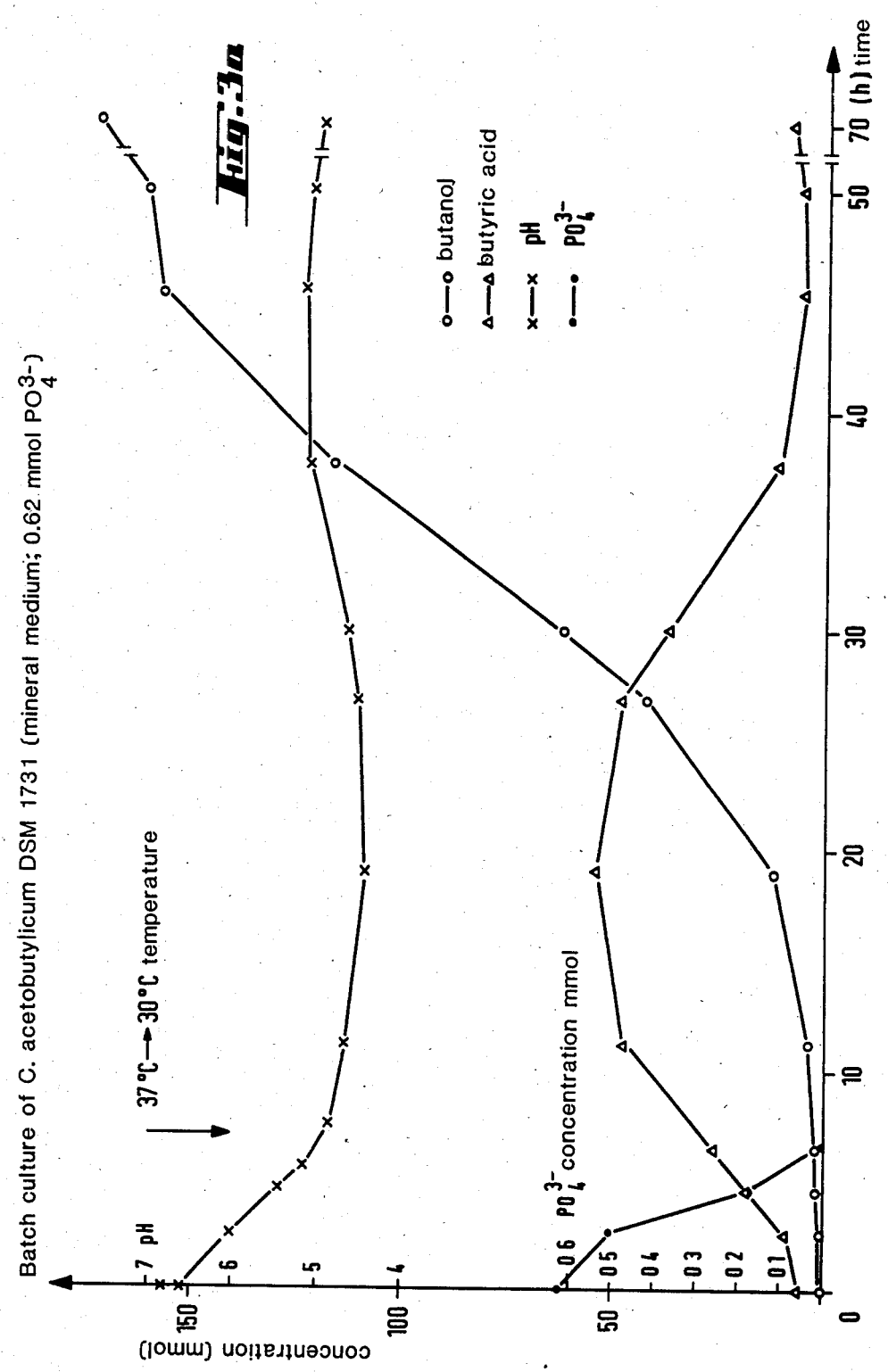

Figure 4A:
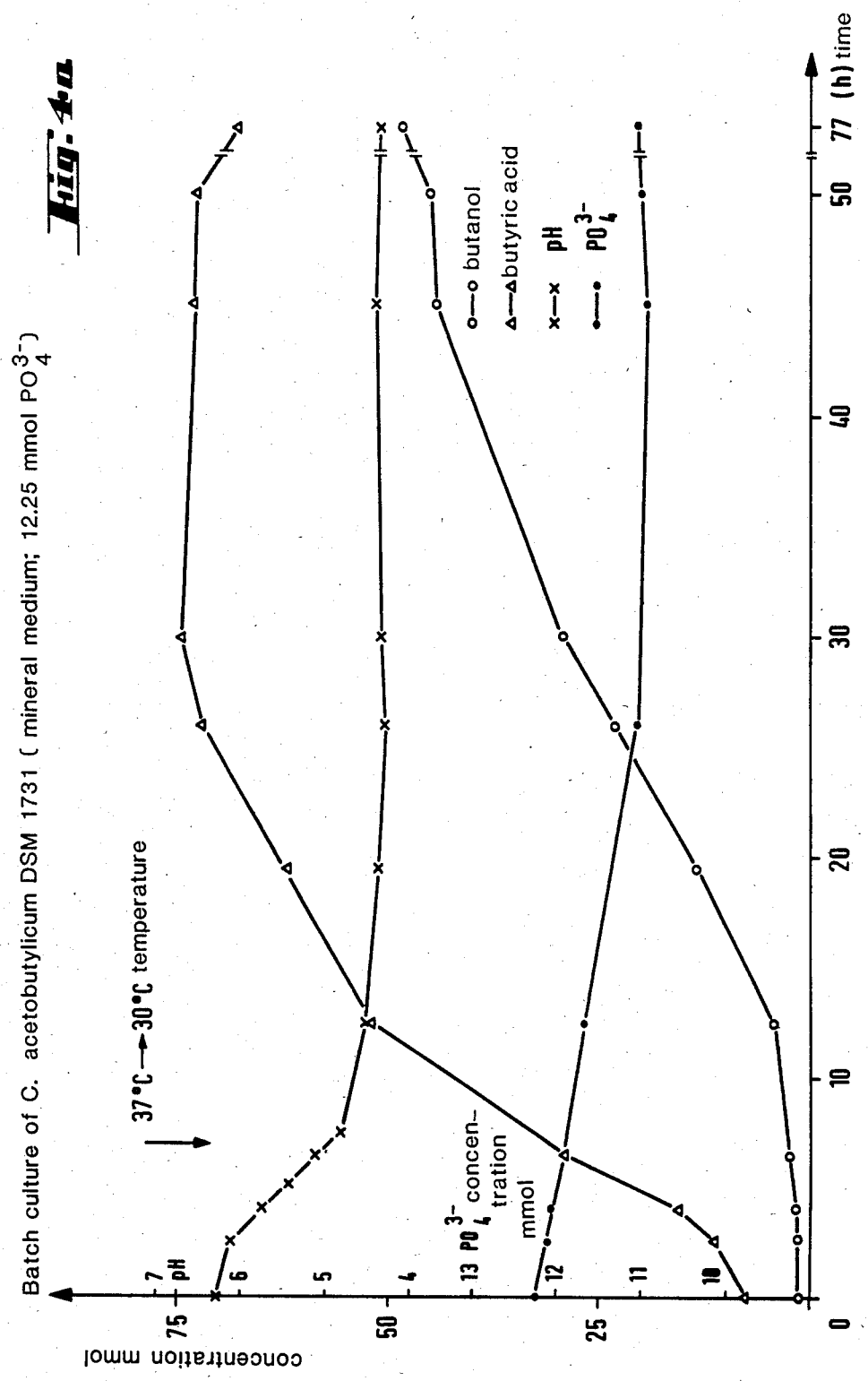

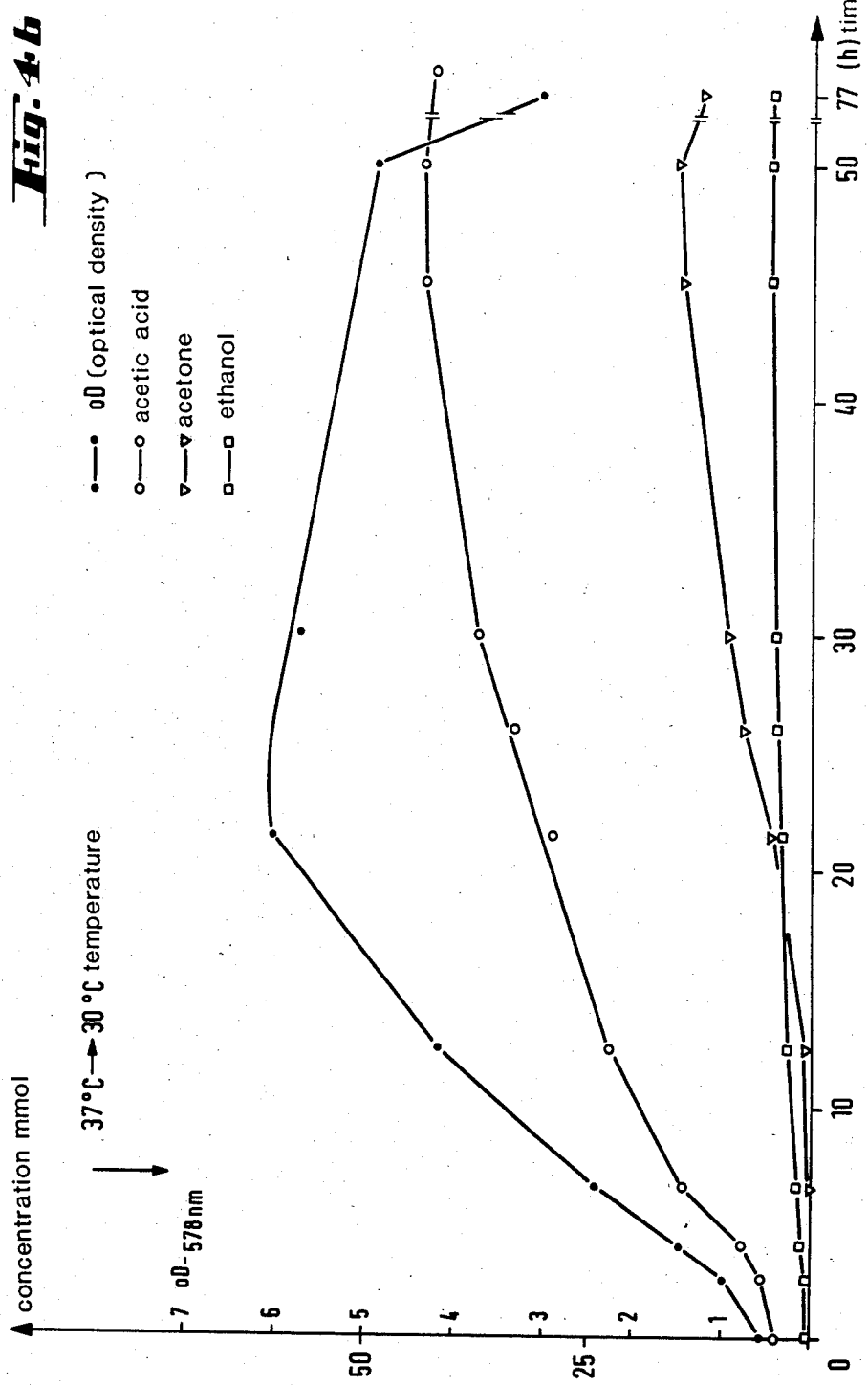
Fig. 4.b

PROCESS FOR FERMENTING CARBOHYDRATE- AND PHOSPHATE-CONTAINING LIQUID MEDIA

This invention relates to a process for fermenting carbohydrate- and phosphate-containing liquid media by means of bacteria capable of forming butanol, acetone and/or ethanol as fermentation products.

Processes for fermenting carbohydrate- and phosphate-containing liquid media by means of bacteria capable of forming butanol, acetone and/or ethanol as fermentation products have been known for decades. Reference is made in this context to the state of the art of which the following examples are cited:

German Pat. Nos. 612 535, 629 679, 635 572, 659 389, 683 198, 700 493, 824 932, 920 724, 941 184 and 941 185.

British Pat. Nos. 4845, 15203, 15204, 319 079, 319 642 and 496 137.

Japanese Pat. No. 61.5797.

U.S. Pat. Nos. 1,315,585, 1,510,526, 1,537,597, 1,538,516, 1,545,694, 1,668,814, 1,822,139, 1,908,361, 1,911,411, 1,913,164, 1,992,921, 2,050,219, 2,089,522, 2,089,562, 2,107,262, 2,113,471, 2,113,472, 2,123,078, 2,132,039, 2,132,358, 2,139,108, 2,139,111, 2,198,104, 2,202,161, 2,260,126, 2,326,425, 2,368,074, 2,369,680, 2,377,197, 2,398,837, 2,433,232, 2,439,791, 2,481,263 and 2,945,786.

Besides U.S. Patent Quarterly, 12 (1932 a) 47–57 and 15 (1932 b) 237.

Bacteria suitable for the purpose are known to those familiar with the art and may be taken, for instance, from the above-mentioned pubications. Among them are, in particular, species and strains of the genus Clostridium, like *Clostridium acetobutylicum, saccharobutylacetonicum, saccharoacetobutylicum* (for instance *saccharoacetobutylicum-alpha, -beta* or *-gamma*), *saccharoperbutylacetonicum, invertoacetobutylicum, propylbutylicum, madisonii, tetrylium* and *saccharobutylacetonicum-liquefaciens* (for instance *saccharobutylacetonicumliquefaciens-alpha, -beta, -gamma* or *-delta*).

Moreover, it is obvious, for instant, from U.S. Pat. No. 2,107,262 that the known process is performed in the presence of soluble mineral phosphate in a range of concentration from 0.01 to 0.15 percent by weight (lines 48–50 on page 1, left column, of the publication). The amount of phosphate to be added is determined in preliminary tests and depends on the amount of soluble mineral phosphate introduced with the fermenting medium (lines 18–27 and 37–39 on page 1, right column, of the publication).

However, the yields of the desired fermentation products butanol, acetone and ethanol obtainable according to the state of the art have not been regarded as satisfactory yet, another unsatisfactory circumstances being that the known state of the art does not cover a continuous process.

In tests supporting this invention it was found that continuous fermentation is possible if phosphate limitation is applied. One embodiment of this invention, therefore, relates to a process for fermentating carbohydrate- and phosphate-containing media by means of bacteria capable of forming butanol, acetone and/or ethanol as fermentation products, the process being characterized by the fact that it is carried out continuously under conditions limited with regard to the dissolved inorganic phosphate or the total phosphate present in the medium.

Now many sugar-containing media show concentrations of dissolved inorganic phosphate or of total phosphate which are above the range suitable for a limitation of phosphate. Such media are used in the process only after having been subjected to a precipitation of phosphate lowering their concentration of inorganic or total phosphate to a point suitable for a limitation of phosphate.

Those familiar with carrying out continuous processes using microorganisms will be able to easily ascertain the range of concentration suitable for phosphate limitation. In doing so they may rely on the following guidelines. If a phosphate concentration is selected which is too high for a phosphate limitation, the phosphate introduced is not consumed. If the phosphate concentration is too low, the optical density will drop and, in the worst of all cases, growth will be inhibited. A concentration of inorganic or total phosphate suitable for a phosphate limitation is, for instance, one in the range from 1.0 to 0.4, preferably from 0.75 to 0.5 mmolar.

According to this invention it has also been found that the formation of the desired fermentation products butanol, acetone and/or ethanol can be continued in a subsequent second process step. It may be carried out continuously like the first process step or, alternatively, batchwise.

A guideline for process conditions is that in the first step (growth step) a flow rate is chosen which ensures that bacterial concentration is kept at a constant, high level, the result being that a steady state is reached and that part of the substrate is already converted into butanol, acetone and/or ethanol. If too high a flow rate is chosen, there will be more cells discharged than formed. Conversely, if the flow rate is too low, cellular growth may temporarily be inhibited. It is the purpose of the second step to achieve the highest possible yield of the desired fermentation products in the shortest time possible. The flow rate should therefore be adjusted accordingly. The following special conditions may, for example, be applied:

First Step

Flow rate 0.04 to 0.20, preferably 0.06 to 0.15 $h^{-1}$, pH 4.0 to 5.0 preferably 4.0 to 4.7, more preferably 4.3 to 4.5; Temperature 30° to 40°, preferably 30° to 37° C.

Second Step pH 3.0 to 5.0, preferably 4.0 to 4.7, more preferably 4.3 to 4.5; Temperature 25° to 39°, preferably 30° to 36°, more preferably 32° to 35° C.

According to another embodiment of this invention a batch process for fermenting carbohydrate- and phosphate-containing liquid media by means of butanol, acetone and/or ethanol as bacteria capable of forming fermentation products is proposed, which is characterized in that (a) a carbohydrate-containing liquid medium is used with a concentration of dissolved inorganic phosphate or of total phosphate present in the medium ranging from 1.0 to 0.4, preferably from 0.75 to 0.5 mmolar, (b) after termination of the growth phase a pH from 3.5 to 5.0 is applied and (c) after termination of the growth phase a reduced temperature is applied.

A guideline for the conditions applicable in the batch process is that the growth phase is carried out at a temperature somewhat higher than that in the subsequent fermentation phase. The fermentation phase begins upon consumption of the phosphate. In the batch process the pH should not be lower than 3.5 and preferably not be lower than 4.0.

With regard to this embodiment it should again be noted that many carbohydrate-containing fermentable media show concentrations of inorganic or total phosphate above the range of 1.0 to 0.4 mmolar indicated. Before such media are used in the batch process of the invention, they are subjected to a phosphate precipitation to lower their concentration of inorganic or total phosphate to a range from 1.0 to 0.4, preferably from 0.75 to 0.5 mmolar.

The four figures and three examples below will more clearly illustrate the process of the invention. The microorganism *Clostridium acetobutylicum* used in the examples is deposited with the German Collection of Microorganisms in Goettingen under No. 1731. The two step continuous process of Example 2 is the preferred process.

(A) CONTINUOUS SINGLE-STEP PROCESS

Example 1

A 250-ml fermentor (designed by GBF in cooperation with P. Ochs) was used which was equipped with a pipe for introducing nitrogen and nutritive solution, a lye dosage system, a pH meter, a magnetic stirrer, a heating jacket and an overflow pipe for gas and cell suspension. An aqueous medium of the following composition was used:

Fermenting medium

All figures referring to one liter:

| | |
|---|---|
| $KH_2PO_4$ | 0.1 g |
| | 0.735 mmol |
| $(NH_4)_2SO_4$ | 2.0 g |
| $FeSO_4 \times 7H_2O$ | 15 mg |
| Glucose $\times$ $H_2O$ | 60 g |
| Salt solution | 10 ml |
| Vitamin solution | 1 ml |
| $Na_2S_2O_4$ | 35 mg |

Vitamin solution

All figures referring to 100 ml:

| | |
|---|---|
| Thiamine dichloride | 200 mg |
| 4-Aminobenzoic acid | 200 mg |
| D(+)-biotin | 10 mg |

Salt solution

All figures referring to one liter:

| | |
|---|---|
| $MgSO_4 \times 7H_2O$ | 10 g |
| NaCl | 1 g |
| $Na_2MoO_4 \times 2H_2O$ | 1 g |
| $CaCl_2 \times 2H_2O$ | 1 g |
| $MnSO_4 \times H_2O$ | 1.5 g |

Figure 1:
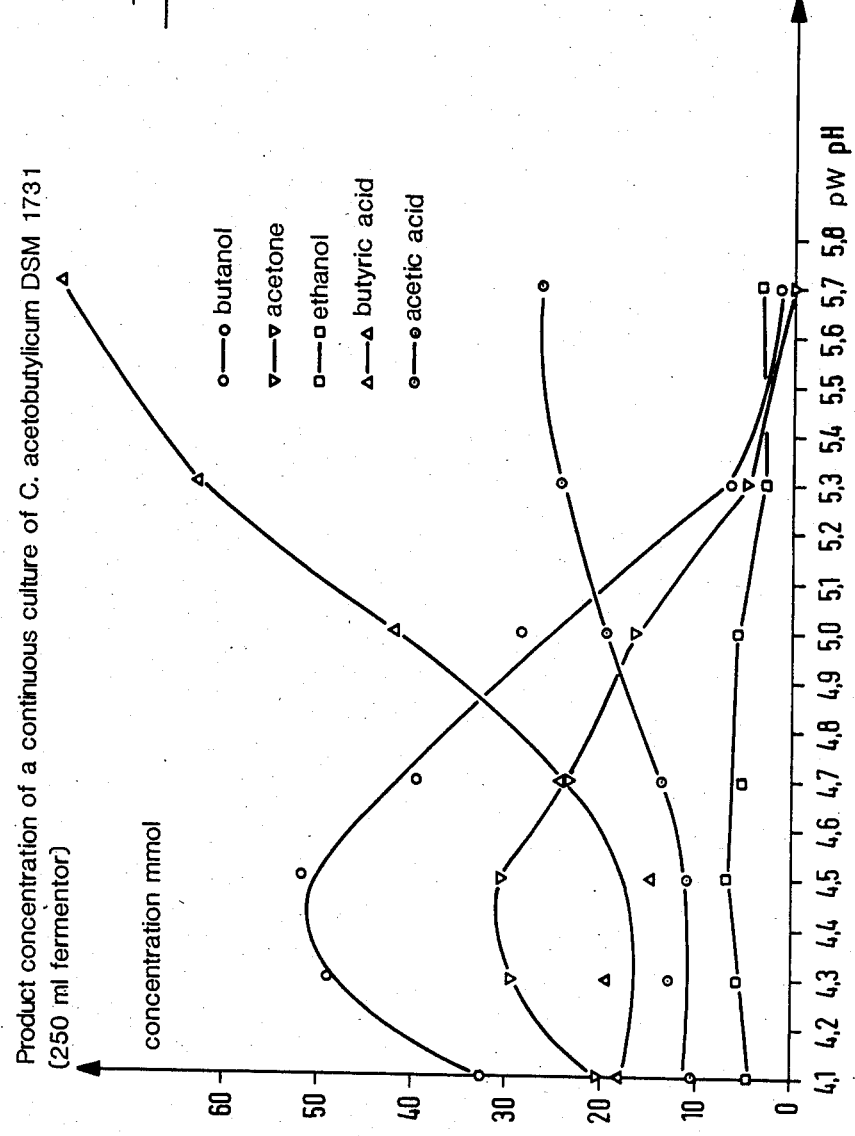

Investigated were the product concentrations with limitation of phosphate at different pH values and a constant flow rate (D) of 0.127 $h^{-1}$. Results are shown in FIG. 1 and Table 1.

TABLE 1

Product and substrate concentrations (mmolar) with limitation of phosphate at various pH values

| pH | Glucose | $PO_4^{3-}$ | $NH_4^+$ | Butanol | Acetone | Ethanol | Butyrate | Acetate |
|---|---|---|---|---|---|---|---|---|
| 5.7 | 175 | 0.090 | 3.4 | 2.3 | 0.3 | 3.2 | 77.2 | 26.5 |
| 5.3 | 174 | 0.086 | 6.5 | 6.4 | 4.5 | 2.9 | 62.6 | 24.3 |
| 5.0 | 179 | 0.079 | 5.9 | 28.4 | 16.8 | 5.5 | 41.7 | 19.5 |
| 4.7 | 177 | 0.075 | 6.5 | 39.5 | 24.1 | 5.1 | 24.5 | 13.5 |
| 4.5 | 170 | 0.075 | 5.9 | 51.5 | 30.1 | 6.9 | 14.8 | 10.8 |
| 4.3 | 175 | 0.055 | 6.4 | 48.7 | 29.8 | 5.5 | 19.9 | 12.6 |
| 4.1 | 200 | 0.071 | 7.3 | 32.4 | 20.6 | 4.5 | 18.1 | 10.9 |

FIG. 1 and Table 1 show that with limitation of phosphate the steady-state concentrations of butanol and acetone increase with decreasing pH and reach a maximum between pH 4.3 and 4.5. From this it is obvious that growing *C. acetobutylicum* cells are capable of forming solvents under the conditions here discovered. Acetone-butanol fermentation may therefore be performed continuously.

Regarding the relatively low amount of substrate converted or the high content of residual sugar it was found that solvent fermentation can be continued in a subsequent step.

(B) CONTINUOUS TWO-STEP PROCESS

Example 2

A 2-liter fermentor (0.9 l culture volume) was used which was connected to a 5-l fermentor (3 l culture volume; Braun Biostat). Equipment (stirring here by paddle wheels) and medium see Example 1.

| Culture conditions in step 1: | |
|---|---|
| pH: | 4.3 |
| T: | 37° C. |
| D: | 0.125 $h^{-1}$ |
| RPM: | 75 |
| Culture conditions in step 2: | |
| pH: | 4.3 |
| T: | variable, see FIG. 2 |
| D: | 0.0375 $h^{-1}$ |
| RPM: | 100 |

Substrate and product concentrations in steps 1 and 2 under the conditions indicated above have been complied in Table 2. FIG. 2 shows solvent production in step 2 in dependence on the temperature. Acid production changed only insignificantly in the temperature range tested. The data given in Table 2 and FIG. 2 show that, with limitation of phosphate, acetone-butanol fermentation involving a high substrate conversion and giving a high yield of the desired products can be performed continuously in a two-step system. The flow rates selected here are merely exemplary. In step 1, D may be varied in the range from 0.04 to 0.20 $h^{-1}$, the product concentration increasing with decreasing flow rate. In step 2 the flow rate must be so selected that the holding time in the fermentor is long enough to ensure a high level of substrate conversion. For C. acetobutylicum DSM 1731 the following rule was found: The slower the flow rate in step 2, the lower is the optimum temperature.

TABLE 2

|  | Substrate and product concentrations in steps 1 and 2 of the continuous system | |
|---|---|---|
|  | Step 1<br>T: 37° C.<br>D: 0.125 h$^{-1}$ | Step 2<br>T: 33° C.<br>D: 0.0375 h$^{-1}$ |
| Butanol | 41.5 mmolar | 142 mmolar |
| Acetone | 25.4 mmolar | 84 mmolar |
| Ethanol | 5 mmolar | 13 mmolar |
| Butyrate | 19.4 mmolar | 11.5 mmolar |
| Acetate | 12 mmolar | 15 mmolar |
| Acetoin | 0.8 mmolar | 2.3 mmolar |
| Glucose | 205 mmolar | 30.5 mmolar |
| PO$_4^{3-}$ | 0.075 mmolar | 0.01 mmolar |
| Substrate consumption | 33% | 90% |
| of which solvent | 69% | 86% |

The higher temperature (37° C.) in step 1 (growth phase) compared to step 2 (33° C., fermentation phase) provided to be advantageous: It allowed faster growth; besides butanol concentration was found to be twice that at, for instance, 30° C. If suitable flow rates are chosen, media with higher substrate concentrations may equally be converted to solvents giving high yields.

It is not necessary to operate the second step continuously; instead it is possible to collect the fermentor outflow of the first step, incubate at, for instance, 30° C. and pH 4.3, and harvest after the residual sugar has been fermented into solvents (duration 1.5 to 2 days).

(C) BATCH PROCESS

Example 3

The principle of phosphate limitation under the above-mentioned conditions in a continuous culture involving controlled acetone-butanol fermentation was found to be applicable also to the batch process.

Figure 3B:
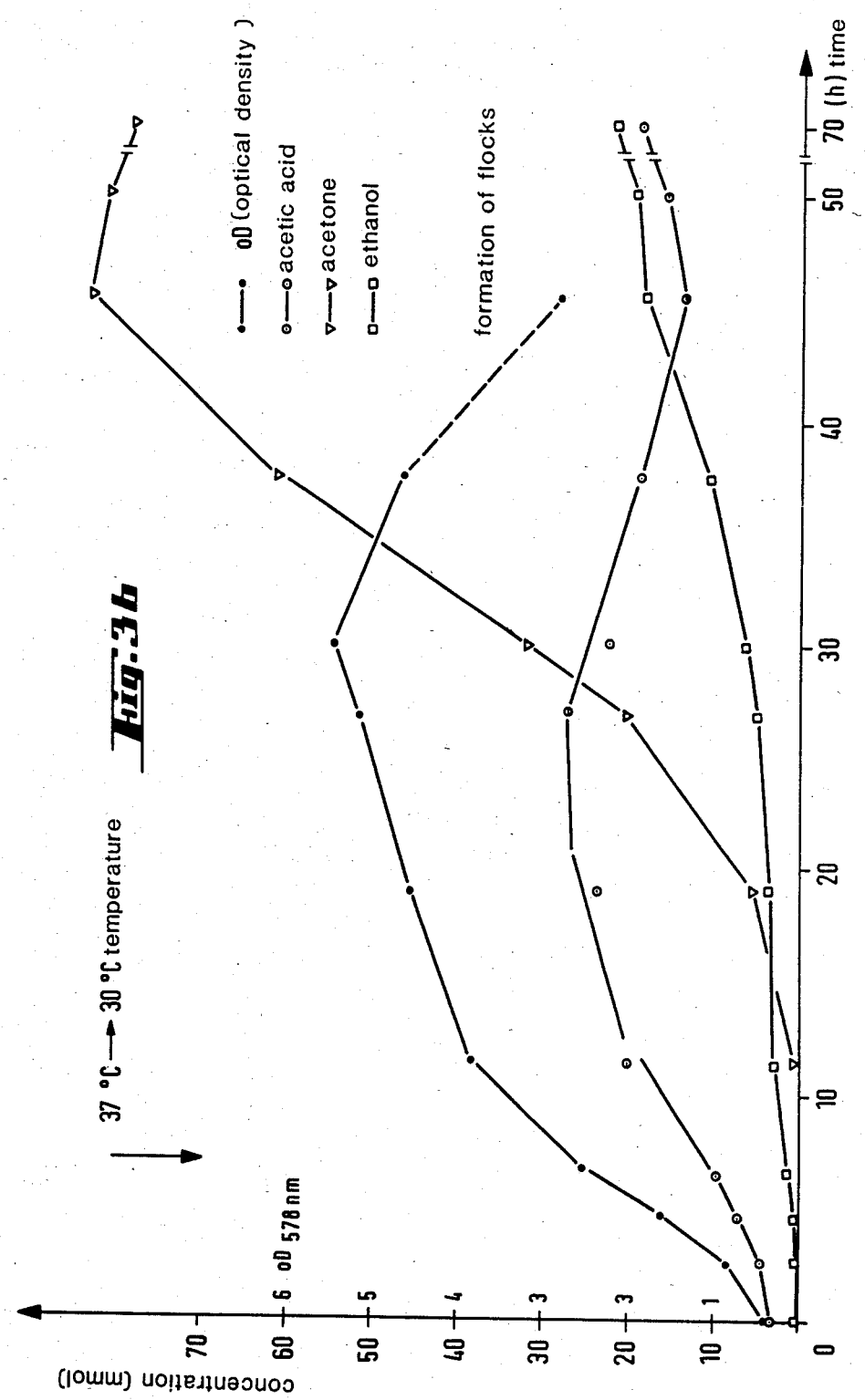

Medium and fermentor were chosen as in Example 2. Cells from step 1 were used as the starting culture. Based on the knowledge gained from the continuous culture, the following experimental procedure was adopted: Incubation during the growth phase was carried out at 37° C. At that time phosphate is still present in the medium. Titration with KOH then prevented an excessively fast drop in pH by which growth would have been impeded. At the beginning of the fermentation phase (pH below 5, no phosphate detectable in the medium) the temperature was adjusted to 30° C. Under these conditions C. acetobutylicum DSM 1731 in a batch culture shows the fermenation pattern plotted in FIG. 3. From FIG. 3 it is obvious that, after consumption of phosphate and decrease of the pH below 5, C. acetobutylicum changes from acid to solvent fermentation fermenting the 6% sugar solution into solvents with a high yield being obtained. FIG. 4 shows the fermentation pattern of a batch culture under otherwise identical conditions but with a 20-fold phosphate concentration. Here no switch from acid to solvent fermentation was observed. While solvent production did start at pH values below 5, the acid produced was not degraded again but rose in concentration. This resulted in a lower yield of solvents as well as in a lower substrate consumption (see Table 3).

TABLE 3

| Substrate and product concentrations in batch cultures with a deficiency and an excess of phosphate after 3 days | | |
|---|---|---|
|  | Deficiency of phosphate | Excess of phosphate |
| Butanol | 175 mmolar | 47 mmolar |
| Aceton | 77* mmolar | 12** mmolar |
| Ethanol | 21.5 mmolar | 4.5 mmolar |
| Butyrate | 8.5 mmolar | 67.5 mmolar |
| Acetate | 18 mmolar | 42 mmolar |
| Acetoin | 9 mmolar | 7.5 mmolar |
| Glucose | 0 mmolar | 129 mmolar |
| PO$_4^{3-}$ | 0 mmolar | 11 mmolar |
| Substrate consumption | 100% | 57% |
| of which solvents | 87.5% | 36% |

*after 2 days 84 mmolar
**after 2 days 15 mmolar

We claim:

1. In a process for producing butanol, acetone and/or ethanol by fermenting carbohydrate and phosphate containing liquid culture medium with bacteria capable of producing butanol, acetone and/or ethanol as fermentation products with a growth step followed by a fermentation step, the improvement comprising maintaining the total soluble phosphate concentration present in the medium between 0.4 and 0.75 mmolar during the fermentation.

2. The process of claim 1 wherein phosphate was precipitated from the liquid culture medium to obtain a total soluble phosphate concentration in the range of 0.4 to 0.75 mmolar at the start of the process.

3. The process of claim 1 wherein the total soluble phosphate concentration is controlled by addition of soluble phosphate.

4. The process of claim 1 wherein the growth step and fermentation step are performed continuously.

5. The process of claim 1 wherein the growth step is performed having a flow rate of 0.04 to 0.20 h$^{-1}$, a pH of 4.0 to 5.0, and a temperature of 30° to 40° C., and the fermentation step is performed having a pH of 3.0 to 5.0 and a temperature of 25° to 39° C.

6. The process of claim 5 wherein after termination of the growth step the pH is adjusted to between 3.5 and 5.0 and the temperature is reduced.

7. The process of claim 1 wherein the growth step is performed continuously and the fermentation step is performed batchwise.

8. The process of claim 1 wherein the growth step is performed with a flow rate of 0.06 to 0.15 h$^{-1}$, a pH of 4.3 to 4.5 and a temperature of 30° to 37° C. and the fermentation step is performed at a pH of 4.3 to 4.5 and a temperature of 32° to 35° C.

* * * * *